(12) United States Patent
Landeta Elorz et al.

(10) Patent No.: US 11,312,762 B2
(45) Date of Patent: Apr. 26, 2022

(54) **ANTIBODIES AND TEST DEVICES FOR THE DETECTION OF BACTERIA OF THE GENUS *CAMPYLOBACTER***

(71) Applicant: CERTEST BIOTEC, S.L., Saragossa (ES)

(72) Inventors: Oscar Landeta Elorz, Saragossa (ES); Yolanda García Miguel, Saragossa (ES); Juan Enrique Martínez Oliván, Saragossa (ES); Beatriz Velasco Michelena, Saragossa (ES)

(73) Assignee: CERTEST BIOTEC, S.L., Saragossa (ES)

(*) Notice: Subject to any disclaimer, the term of this patent is extended or adjusted under 35 U.S.C. 154(b) by 81 days.

(21) Appl. No.: 16/652,951

(22) PCT Filed: Oct. 2, 2018

(86) PCT No.: PCT/EP2018/076857
§ 371 (c)(1),
(2) Date: Apr. 1, 2020

(87) PCT Pub. No.: WO2019/068733
PCT Pub. Date: Apr. 11, 2019

(65) Prior Publication Data
US 2020/0317756 A1 Oct. 8, 2020

(30) Foreign Application Priority Data

Oct. 2, 2017 (EP) .................................. 17382654

(51) Int. Cl.
*C07K 16/12* (2006.01)
*G01N 33/543* (2006.01)
*G01N 33/569* (2006.01)
*G01N 33/58* (2006.01)

(52) U.S. Cl.
CPC ......... *C07K 16/121* (2013.01); *G01N 33/543* (2013.01); *G01N 33/56922* (2013.01); *G01N 33/585* (2013.01); *C07K 2317/565* (2013.01)

(58) Field of Classification Search
None
See application file for complete search history.

(56) References Cited

U.S. PATENT DOCUMENTS

| 6,569,635 B1 | 5/2003 | Blum |
| 2011/0027261 A1 | 2/2011 | Leung et al. |
| 2011/0076723 A1 | 3/2011 | Min et al. |
| 2015/0166661 A1 | 6/2015 | Chen et al. |

FOREIGN PATENT DOCUMENTS

| CN | 106810609 A | 6/2017 |
| JP | 2009-77658 A | 4/2009 |
| JP | 5467228 B2 | 4/2014 |
| WO | 2008/008092 A2 | 1/2008 |

OTHER PUBLICATIONS

Edwards et al. J. Mol. Biol. (2003) 334, 103-118.*
Ferrara et al. mAbs, 7:1, 32-41, 2015.*
Bessède et al., "New Methods for Detection of *Campylobacters* in Stool Samples in Comparison to Culture," *J.Clin. Microb.* 49(3):941-944, 2011.
Couturier et al., "Detection of non-*jejuni* and -*coli Campylobacter* Species from Stool Specimens with an Immunochromatographic Antigen Detection Assay," *J. Clin Microbiol.* 51(6): 1935-1937, 2013.
Granato et al., "Comparison of Premier CAMPY Enzyme Immunoassay (EIA), ProSpecT *Campylobacter* EIA, and ImmunoCard STAT! CAMPY Tests with Culture for Laboratory Diagnosis of *Campylobacter* Enteric Infections," *Journal of Clinical Microbiology* 48(11):4022-4027, 2010.
Ishikawa et al., "The Iron-Binding Protein Dps Confers Hydrogen Peroxide Stress Resistance to *Campylobacter jejuni*," *Journal of Bacteriology* 185(3):1010-1017, 2003.
Piao et al., "Tissue Binding Patterns and In Vitro Effects of *Campylobacter jejuni* DNA-Binding Protein from Starved Cells," *Neurochemical Research* 36(1):58-66, 2010.

* cited by examiner

*Primary Examiner* — Oluwatosin A Ogunbiyi
(74) *Attorney, Agent, or Firm* — Seed Intellectual Property Law Group LLP

(57) ABSTRACT

The present invention can be included in the field of diagnostics. The present invention provides hybridomas, antibodies and test devices for the detection of bacteria of the genus *Campylobacter* in a sample. Further, the present invention discloses the uses of the antibodies and a method for detecting bacteria of the genus *Campylobacter*. The antibodies of the present invention are specific for DNA-Binding Protein from Starved Cells (Dps) and provide less false positives and a higher sensitivity when used in an immunochromatographic test device than other antibodies used to detect bacteria of the genus *Campylobacter*.

12 Claims, 1 Drawing Sheet

Specification includes a Sequence Listing.

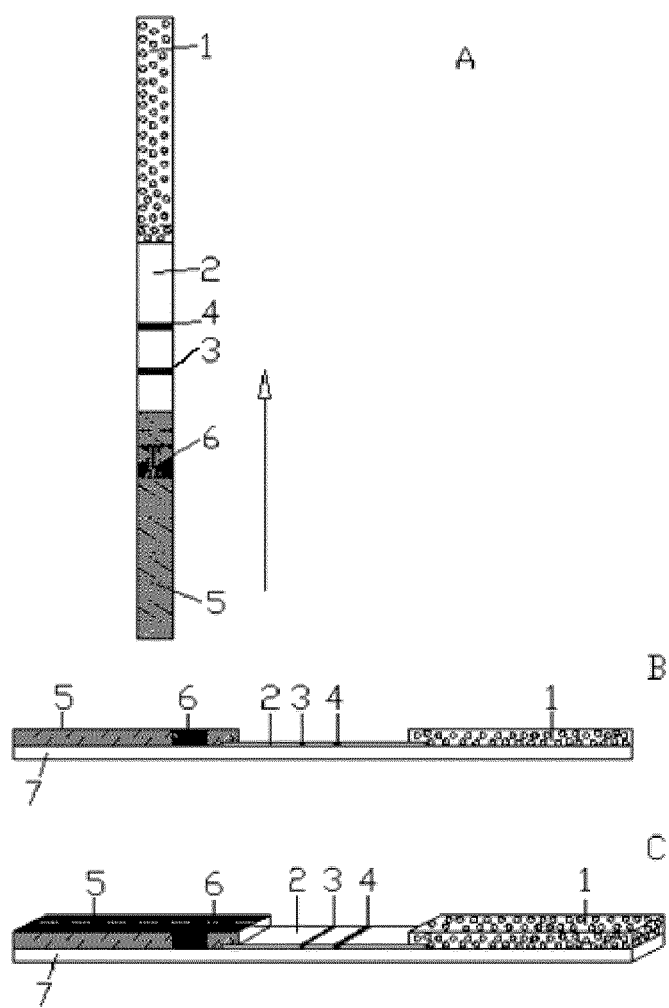

SEQUENCE LISTING

```
<160> NUMBER OF SEQ ID NOS: 12

<210> SEQ ID NO 1
<211> LENGTH: 12
<212> TYPE: PRT
<213> ORGANISM: Artificial Sequence
<220> FEATURE:
<223> OTHER INFORMATION: Light chain varialble region LCDR1

<400> SEQUENCE: 1

Ser Ala Ser Ser Ser Val Ser Ser Tyr Leu His
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Light chain variable region LCDR2

<400> SEQUENCE: 2

Arg Thr Ser Asn Leu Ala Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Light chain variale region LCDR3

<400> SEQUENCE: 3

Gln Gln Trp Ser Gly Tyr Pro Phe Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Heavy chain variable region HCDR1

<400> SEQUENCE: 4

Gly Phe Ser Leu Thr Ser Ser Gly Val His
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Heavy chain varialble region HCDR2

<400> SEQUENCE: 5

Val Ile Trp Arg Gly Gly Ser Thr Asp Tyr Asn Ala Ala Phe Met Ser
```

<210> SEQ ID NO 6
<211> LENGTH: 13
<212> TYPE: PRT
<213> ORGANISM: Artificial Sequence
<220> FEATURE:
<223> OTHER INFORMATION: Heavy chain variable region HCDR3

<400> SEQUENCE: 6

Asn Tyr Tyr Tyr Gly Thr Ser Pro Asp Tyr Phe Asp Tyr
1               5                   10

<210> SEQ ID NO 7
<211> LENGTH: 108
<212> TYPE: PRT
<213> ORGANISM: Artificial Sequence
<220> FEATURE:
<223> OTHER INFORMATION: Light chain variable region fragment of
      CL30Camp

<400> SEQUENCE: 7

Glu Asn Val Leu Thr Gln Ser Pro Ala Ile Met Ala Ala Ser Leu Gly
1               5                   10                  15

Gln Lys Val Thr Met Thr Cys Ser Ala Ser Ser Ser Val Ser Ser Ser
            20                  25                  30

Tyr Leu His Trp Tyr Gln Gln Lys Ser Gly Ala Ser Pro Lys Pro Leu
        35                  40                  45

Ile His Arg Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Asp Ala Thr Tyr Tyr Cys Gln Gln Trp Ser Gly Tyr Pro
                85                  90                  95

Phe Thr Phe Gly Gly Gly Thr Lys Leu Glu Ile Lys
            100                 105

<210> SEQ ID NO 8
<211> LENGTH: 121
<212> TYPE: PRT
<213> ORGANISM: Artificial Sequence
<220> FEATURE:
<223> OTHER INFORMATION: Heavy chain varialbe region fragment of
      CL30Camp

<400> SEQUENCE: 8

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Ser
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Pro Asp Asp Thr Ala Ile Tyr Tyr Cys Ala
                85                  90                  95

Lys Asn Tyr Tyr Tyr Gly Thr Ser Pro Asp Tyr Phe Asp Tyr Trp Gly
            100                 105                 110

-continued

Gln Gly Thr Thr Leu Thr Val Ser Ser
            115                 120

<210> SEQ ID NO 9
<211> LENGTH: 215
<212> TYPE: PRT
<213> ORGANISM: Artificial Sequence
<220> FEATURE:
<223> OTHER INFORMATION: Light chain of CL30Camp sequence

<400> SEQUENCE: 9

Glu Asn Val Leu Thr Gln Ser Pro Ala Ile Met Ala Ala Ser Leu Gly
1               5                   10                  15

Gln Lys Val Thr Met Thr Cys Ser Ala Ser Ser Val Ser Ser Ser
            20                  25                  30

Tyr Leu His Trp Tyr Gln Gln Lys Ser Gly Ala Ser Pro Lys Pro Leu
            35                  40                  45

Ile His Arg Thr Ser Asn Leu Ala Ser Gly Val Pro Ala Arg Phe Ser
        50                  55                  60

Gly Ser Gly Ser Gly Thr Ser Tyr Ser Leu Thr Ile Ser Ser Val Glu
65                  70                  75                  80

Ala Glu Asp Asp Ala Thr Tyr Tyr Cys Gln Gln Trp Ser Gly Tyr Pro
                85                  90                  95

Phe Thr Phe Gly Gly Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215

<210> SEQ ID NO 10
<211> LENGTH: 445
<212> TYPE: PRT
<213> ORGANISM: Artificial Sequence
<220> FEATURE:
<223> OTHER INFORMATION: Heavy chain of CL30Camp sequence

<400> SEQUENCE: 10

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Ser
            20                  25                  30

Gly Val His Trp Val Arg Gln Ser Pro Gly Lys Gly Leu Glu Trp Leu
            35                  40                  45

Gly Val Ile Trp Arg Gly Gly Ser Thr Asp Tyr Asn Ala Ala Phe Met
        50                  55                  60

Ser Arg Leu Ser Ile Thr Lys Asp Asn Ser Lys Ser Gln Val Phe Phe
65                  70                  75                  80

Lys Met Asn Ser Leu Gln Pro Asp Asp Thr Ala Ile Tyr Tyr Cys Ala
                85                  90                  95

Lys Asn Tyr Tyr Tyr Gly Thr Ser Pro Asp Tyr Phe Asp Tyr Trp Gly
            100                 105                 110

Gln Gly Thr Thr Leu Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445

<210> SEQ ID NO 11
<211> LENGTH: 149
<212> TYPE: PRT
<213> ORGANISM: Artificial Sequence
<220> FEATURE:
<223> OTHER INFORMATION: DNA binding protein from starved cells
      of Campylobacter jejuni

```
<400> SEQUENCE: 11

Met Ser Val Thr Lys Gln Leu Leu Gln Met Gln Ala Asp Ala His His
1               5                  10                  15

Leu Trp Val Lys Phe His Asn Tyr His Trp Asn Val Lys Gly Leu Gln
                20                  25                  30

Phe Phe Ser Ile His Glu Tyr Thr Glu Lys Ala Tyr Glu Glu Met Ala
            35                  40                  45

Glu Leu Phe Asp Ser Cys Ala Glu Arg Val Leu Gln Leu Gly Glu Lys
        50                  55                  60

Ala Ile Thr Cys Gln Lys Val Leu Met Glu Asn Ala Lys Ser Pro Lys
65                  70                  75                  80

Val Ala Lys Asp Cys Phe Thr Pro Leu Glu Val Ile Glu Leu Ile Lys
                85                  90                  95

Gln Asp Tyr Glu Tyr Leu Leu Ala Glu Phe Lys Lys Leu Asn Glu Ala
            100                 105                 110

Ala Glu Lys Glu Ser Asp Thr Thr Ala Ala Phe Ala Gln Glu Asn
            115                 120                 125

Ile Ala Lys Tyr Glu Lys Ser Leu Trp Met Ile Gly Ala Thr Leu Gln
            130                 135                 140

Gly Ala Cys Lys Met
145

<210> SEQ ID NO 12
<211> LENGTH: 149
<212> TYPE: PRT
<213> ORGANISM: Artificial Sequence
<220> FEATURE:
<223> OTHER INFORMATION: DNA binding protein from starved cells
      of Campylobacter coli

<400> SEQUENCE: 12

Met Ser Val Thr Lys Gln Leu Leu Gln Met Gln Ala Asp Ala His His
1               5                  10                  15

Leu Trp Val Lys Phe His Asn Tyr His Trp Asn Val Lys Gly Leu Gln
                20                  25                  30

Phe Tyr Ser Ile His Glu Tyr Thr Glu Lys Ala Tyr Glu Glu Met Ala
            35                  40                  45

Glu Leu Phe Asp Asn Cys Ala Glu Arg Ala Leu Gln Leu Gly Glu Lys
        50                  55                  60

Ala Ile Thr Cys Gln Lys Thr Leu Met Glu Asn Ala Lys Ser Pro Lys
65                  70                  75                  80

Val Glu Lys Asp Cys Phe Thr Pro Val Glu Val Met Glu Leu Ile Lys
                85                  90                  95

Lys Asp Tyr Glu Tyr Leu Leu Ala Glu Phe Lys Lys Leu Asn Glu Glu
            100                 105                 110

Ala Glu Lys Ala Ser Asp Thr Thr Ala Ala Phe Ala Gln Glu Asn
            115                 120                 125

Ile Ala Lys Tyr Glu Lys Ser Leu Trp Met Leu Ala Ser Val Leu Gln
            130                 135                 140

Asn Thr Cys Lys Met
145
```

ANTIBODIES AND TEST DEVICES FOR THE DETECTION OF BACTERIA OF THE GENUS *CAMPYLOBACTER*

TECHNICAL FIELD

The present invention can be included in the field of diagnostics. Specifically, the present invention provides an antibody which is specific for the DNA-Binding Protein from Starved Cells (Dps) of bacteria of the genus *Campylobacter* and a hybridoma which produces said antibody. The antibody can be used in an immunochromatographic test device and in a method for detecting bacteria of the genus *Campylobacter*.

BACKGROUND ART

In humans, 85% to 95% of infections by the *Campylobacter* species involve *Campylobacter jejuni*, while *Campylobacter coli* is involved in a majority of the other cases. *C. jejuni* is one of the most common causes of food poisoning in the United States and in Europe. The vast majority of cases occur as isolated events, not as part of recognized outbreaks. Active surveillance through the Foodborne Diseases Active Surveillance Network (FoodNet) indicates that about 14 cases are diagnosed each year for each 100,000 persons in the population. The European Food Safety Authority estimated in 2011 that there are approximately nine million cases of human campylobacteriosis per year in the European Union.

Food poisoning caused by *Campylobacter* species can be severely debilitating, but is rarely life-threatening. It has been linked with subsequent development of Guillain-Barré syndrome, which usually develops two to three weeks after the initial illness. Individuals with recent *C. jejuni* infections develop Guillain-Barré syndrome at a rate of 0.3 per 1000 infections, about 100 times more often than the general population.

Thus, there is currently a need to detect species of the genus *Campylobacter*. Previous devices for the detection of *Campylobacter jejuni* in stool samples have involved the use of immunochromatographic test devices which detect a surface protein of *Campylobacter jejuni* (JP5467228B2; JP 2009077658 (A); Granato et al., 2010. *Comparison of Premier CAMPY Enzyme Immnunoassay (EIA), ProSpecT Campylobacter EIA, and Immuno Card STAT! CAMPY test with culture for laboratory diagnosis of campylobacter enteric infections*. J. Clin. Microb. 4022-4027). However, current detection devices suffer from a lack of specificity which can cause false positives (Bessede et al., 2011. *New Methods for Detection of Campylobacters in Stool samples in comparison to culture*. J. Clin. Microb. 941-944; Couturier et al., 2003. *Detection of non-jejuni and campylobacter species from stool specimens with an immunochromatographic antigen detection assay*. J. Clin Microbiol. (6): 1935-7). Further, these devices can suffer from a lack of sensitivity.

There is a need for a test device which produces less false positives and which is more sensitive than the test devices currently available. Through the use of an antibody which binds to the DNA-Binding Protein from Starved Cells (Dps) of *C. jejuni* and *C. coli*, the inventors of the present application have developed a test device which produces less false positives and is more sensitive than other devices currently available.

FIGURES

FIG. 1: Diagram of the immunochromatographic test device. A) Bird's-eye view of the immunochromatographic test device in the form of a strip. The test device comprises the following elements: an absorbent material (1), a support membrane (2) with a detection section (3) and a control section (4), a sample addition section (5) and a section of the device which comprises the labeled antibody (6). The arrow indicates the flow direction. B) Side-view of the immunochromatographic test device in the form of a strip. The test device further comprises a plastic support (7). (c) Angled side-view of the immunochromatographic test device.

SUMMARY OF THE INVENTION

The present invention provides an antibody which specifically binds Dps, a hybridoma which produces the antibody of the present invention and an immunochromatographic test device comprising: (a) a first antibody which specifically binds to Dps, (b) a second antibody which specifically binds to Dps, and (c) a support membrane, wherein the first antibody is immobilized on the support membrane and the second antibody is labeled. Further, the present invention provides a method for detecting bacteria of the genus *Campylobacter* in an isolated sample which comprises contacting the sample with the test device of the present invention, the use of the antibody of the present invention for the detection of bacteria of the genus *Campylobacter* and the use of the antibody of the present invention for the manufacture of an immunoassay test device.

DETAILED DESCRIPTION OF THE INVENTION

Antibody

In a first aspect, the present invention provides an antibody which specifically binds Dps.

As used herein, the term "antibody" refers to a protein comprising at least one immunoglobulin variable domain sequence. The term antibody includes, for example, full-length, mature antibodies and antigen-binding fragments of an antibody. For example, an antibody molecule can include a heavy (H) chain variable domain sequence (abbreviated herein as VH), and a light (L) chain variable domain sequence (abbreviated herein as VL). In another example, an antibody includes two heavy (H) chain variable domain sequences and two light (L) chain variable domain sequence, thereby forming two antigen binding sites, such as Fab, Fab', F(ab')2, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The antibodies of the present invention can be monoclonal or polyclonal. The antibody can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) Science 242:423-426; and Huston et al. (1988) Proc. Natl. Acad. Sci. USA 85:5879-5883); (viii) a single domain antibody. These antibody fragments are obtained using conventional techniques known to those with skill in the art, and the fragments are screened for utility in the same manner as are intact antibodies.

The term "antibody" includes intact molecules. Constant regions of the antibodies can be altered, e.g., mutated, to modify the properties of the antibody (e.g., to increase or decrease one or more of: Fc receptor binding, antibody glycosylation, the number of cysteine residues, effector cell function or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarily determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) J. Mol. Biol. 196:901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme). As used herein, the CDRs defined according the "Chothia" number scheme are also sometimes referred to as "hypervariable loops".

The terms "monoclonal antibody" as used herein refers to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

The antibody thereof can be a polyclonal or a monoclonal antibody. In other embodiments, the antibody can be recombinantly produced, e.g., produced by phage display or by combinatorial methods. Preferably, the antibody is a monoclonal antibody.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immuno! 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention.

Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

A humanized or CDR-grafted antibody will have at least one or two but generally all three recipient CDRs (of heavy and or light immunoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to Dsp. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor". In one embodiment, the donor immunoglobulin is a non-human (e.g., rodent) immunoglobulin. The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (see e.g., Winnaker, From Genes to Clones (Verlagsgesellschaft, Weinheim, Germany 1987)). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art (see e.g., Morrison, S. L., 1985, Science 229:1202-1207, by Oi et al., 1986, BioTechniques 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 Nature 321:552-525; Verhoeyan et al. 1988 Science 239:1534; Beidler et al. 1988 J. Immunol. 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Criteria for selecting amino acids from the donor are described in U.S. Pat. No. 5,585,089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody can be a single chain antibody. A single-chain antibody (scFV) may be engineered (see, for example, Colcher, D. et al. (1999) Ann N Y Acad Sci 880:263-80; and Reiter, Y. (1996) Clin Cancer Res 2:245-52). The single chain antibody can be dimerized or multimerized to generate multivalent antibodies having specificities for different epitopes of the same target protein.

In yet other embodiments, the antibody has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has effector function and can fix complement. In other embodiments the antibody does not recruit effector cells or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

An antibody can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

An antibody molecules may be conjugated to another molecular entity, typically a label or a therapeutic (e.g., a cytotoxic or cytostatic) agent or moiety. Radioactive isotopes can be used in diagnostic or therapeutic applications. Such radioactive isotopes include, but are not limited to iodine (131I or 125I), yttrium (90Y), lutetium (177Lu), actinium (225Ac), praseodymium, astatine (211At), rhenium (186Re), bismuth (212Bi or 213Bi), indium (111In), technetium (99 mTc), phosphorus (32P), rhodium (188Rh), sulfur (35S), carbon (14C), tritium (3H), chromium (51Cr), chlorine (36Cl), cobalt (57Co or 58Co), iron (59Fe), selenium (75Se), or gallium (67Ga). Radioisotopes useful as labels, e.g., for use in diagnostics, include iodine (131I or 125I), indium (111In), technetium (99mTc), phosphorus (32P), carbon (14C), and tritium (3H), or one or more of the therapeutic isotopes listed above.

The invention provides radiolabeled antibody molecules and methods of labeling the same. In one embodiment, a method of labeling an antibody molecule is disclosed. The method includes contacting an antibody molecule, with a chelating agent, to thereby produce a conjugated antibody. The conjugated antibody is radiolabeled with a radioisotope, e.g., 111Indium, 90Yttrium and 177Lutetium, to thereby produce a labeled antibody molecule.

The term "Dps" or "DNA-Binding Protein from Starved Cells" refers to a protein from the ferritin superfamily which may be characterized by the entries under the accession number QOP891 (*C. jejuni*) and/or AOAOQ2JBU3 (*C. coli*) in the UniProtKB database. Dps preferably refers to the Dps of *C. jejuni* and/or the Dps of *C. coli*.

In a preferred embodiment, the antibody does not produce any signal in a sandwich immunoassay in the absence of Dps and/or the antibody can detect less than 3 ng/ml of Dps when used in a sandwich immunoassay. Preferably, the sandwich immunoassay is an immunochromatographic assay. More preferably, the two antibodies used in the sandwich immunoassay are the antibody of the present invention. In Table 1 of the Examples, CL30Camp in combination with CL30Camp produces no background noise when a sample comprising PBS+0.1% BSA is applied to the immunochromatographic test device. In Tables 2 and 3 of the Examples, the immunochromatographic test device is shown to detect less than 3 ng/ml of Dps from *C. jejuni* and *C. coli*.

In a preferred embodiment, the antibody can detect less than 3 ng/ml of Dps when used in a sandwich immunoassay, preferably an immunochromatographic assay. Preferably, the antibody can detect less than 2 or 1.5 ng/ml of Dps. More preferably, the antibody can detect less than 1 ng/ml of Dps.

In a preferred embodiment, the antibody is obtained or obtainable by immunizing an animal with native or recombinant Dps. In an alternative embodiment, the antibody is obtained or obtainable by immunizing an animal with an immunogen that comprises SEQ ID NO: 11 and/or SEQ ID NO: 12. In a preferred embodiment, the antibody specifically binds to SEQ ID NO: 11 and/or SEQ ID NO: 12.

SEQ ID NO: 11 is the Dps of *C. jejuni* and has the following sequence:

MSVTKQLLQMQADAHHLWVKFEINYHWNVKGLQFFSIHEYTEKAYEEMAE

LFDSCAERVLQLGEKAITCQKVLMENAKSPKVAKDCFTPLEVIELIKQDY

EYLLAEFKKLNEAAEKESDTTTAAFAQENIAKYEKSLWMIGATLQGACKM

SEQ ID NO: 12 is the Dps of *C. coli* and has the following sequence:

MSVTKQLLQMQADAHHLWVKFHNYHWNVKGLQFYSIHEYTEKAYEEMAEL

FDNCAERALQLGEKAITCQKTLMENAKSPKVEKDCFTPVEVMELIKKDYE

YLLAEFKKLNEEAEKASDTTTAAFAQENIAKYEKSLWMLASVLQNTCKM

In a preferred embodiment, the antibody comprises a light chain variable region (VL) and a heavy chain variable region (VH), wherein said VL comprises LCDR1, LCDR2 and LCDR3 polypeptides and VH comprises HCDR1, HCDR2 and HCDR3 polypeptides, wherein LCDR1 is SASSSVSS-SYLH (SEQ ID NO: 1), LCDR2 is RTSNLAS (SEQ ID NO: 2), LCDR3 is QQWSGYPFT (SEQ ID NO: 3), HCDR1 is GFSLTSSGVH (SEQ ID NO: 4), HCDR2 is VIWRGGST-DYNAAFMS (SEQ ID NO: 5) and HCDR3 is NYYYGT-SPDYFDY (SEQ ID NO: 6).

SEQ ID NO: 7 is the VL fragment present in CL30Camp and has the following sequence:

ENVLTQSPAINIAASLGQKVTMTCSASSSVSSSYLHWYQQKSGASPKPLI

HRTSNLASGVPARFSGSGSGTSYSLTISSVEAEDDATYYCQQWSGYPFTF

GGGTKLEIK

SEQ ID NO: 8 is the VH fragment present in CL30Camp and has the following sequence:

QVQLKQSGPGLVQPSQSLSITCTVSGFSLTSSGVHWVRQSPGKGLEWLGV

IWRGGSTDYNAAFMSRLSITKDNSKSQVFFKMNSLQPDDTAIYYCAKNYY

YGTSPDYFDYWGQGTTLTVSS

In a preferred embodiment, the antibody comprises a VL and a VH, wherein the VL is SEQ ID NO: 7 and the VH is SEQ ID NO: 8.

SEQ ID NO: 9 is the LC present in CL30Camp and has the following sequence:

ENVLTQSPAIMAASLGQKVTMTCSASSSVSSSYLHWYQQKSGASPKPLIH

RTSNLASGVPARFSGSGSGTSYSLTISSVEAEDDATYYCQQWSGYPFTFG

GGTKLEIKRADAAPTVSIFPPSSEQLTSGGASVVCFLNNFYPKDINVKWK

IDGSERQNGVLNSWTDQDSKDSTYSMSSTLTLTKDEYERHNSYTCEATHK

TSTSPIVKSFNRNEC

SEQ ID NO: 10 is the HC present in CL30Camp and has the following sequence:

QVQLKQSGPGLVQPSQSLSITCTVSGFSLTSSGVHWVRQSPGKGLEWLGV

IWRGGSTDYNAAFMSRLSITKDNSKSQVFFKMNSLQPDDTAIYYCAKNYY

-continued

YGTSPDYFDYWGQGTTLTVSSAKTTPPSVYPLAPGSAAQTNSMVTLGCLV

KGYFPEPVTVTWNSGSLSSGVHTFPAVLQSDLYTLSSSVTVPSSTWPSET

VTCNVAHPASSTKVDKKIVPRDCGCKPCICTVPEVSSVFIFPPKPKDVLT

ITLTPKVTCVVVDISKDDPEVQFSWFVDDVEVHTAQTQPREEQFNSTFRS

VSELPIMHQDWLNGKEFKCRVNSAAFPAPIEKTISKTKGRPKAPQVYTIP

PPKEQMAKDKVSLTCMITDFFPEDITVEWQWNGQPAENYKNTQPIMDTDG

SYFVYSKLNVQKSNWEAGNTFTCSVLHEGLHNHHTEKSLSHSPGK

In a preferred embodiment, the antibody comprises a light chain (LC) and a heavy chain (HC), and the LC is SEQ ID NO: 9 and the HC is SEQ ID NO: 10. In a preferred embodiment, the antibody comprises two LCs and two HCs, wherein the LCs are SEQ ID NO: 9 and the HCs are SEQ ID NO: 10.

In a preferred embodiment, the antibody is a monoclonal antibody.

The anti-Dps antibody may be labeled. Labeling may be performed by using any ordinary method. The labeling substance used for labeling is preferably an insoluble particle. Examples of suitable particles include: colored synthetic polymer particles obtained by dye-molecule labeling synthetic polymers such as latex, polyethylene, polypropylene, polystyrene, a styrene-butadiene copolymer, polyvinyl chloride, polyvinyl acetate, polyacrylamide, polymethacrylate, a styrene-methacrylate copolymer, polyglycidyl methacrylate, and an acrolein-ethylene glycol dimethacrylate copolymer; colloidal metal particles (gold, silver, copper, iron, platinum, palladium, and a mixture thereof (for example, a mixture of gold and platinum, a mixture of gold and silver, and a mixture of palladium and platinum)); and red blood cells. Preferably, the particle allows a change to be easily and quickly checked by visual inspection. Colored synthetic polymer particles or colloidal metal particles may be used for this purpose. The particles have a particle size of, for example, 15 to 400 nm, preferably 100 to 400 nm for colored synthetic polymer particles or 30 to 80 nm for colloidal metal particles. The colloidal metal particles may be commercially available products, or may be prepared by using an ordinary method.

In the case of labeling with colloidal metal particles, 0.1 to 100 mg, preferably 0.5 to 20 mg of anti-Dps antibody is typically added to 1 L of a colloidal metal particle solution (typically, an absorbance of about 2.0 at 540 nm), and the mixture is refrigerated, or stirred at room temperature for 5 minutes to 24 hours. After blocking with bovine serum albumin (BSA; typically 0.01 to 10 g, preferably 0.1 to 2 g), the solution is centrifuged, and the resulting precipitate is obtained as anti-Dps antibodies labeled with the colloidal metal particles.

In a preferred embodiment, the antibody is labeled with a colored synthetic polymer particle and/or a colloidal metal particle. Preferably the colored synthetic polymer particle comprises polystyrene.

Immunochromatographic Test Device

In a second aspect, the present invention provides an immunochromatographic test device comprising: (a) a first antibody which specifically binds to Dps, (b) a second antibody which specifically binds to Dps, and (c) a support membrane, wherein the first antibody is immobilized on the support membrane and the second antibody is labeled.

As used herein, the term "immobilize" refers to attaching an antibody on a support such as a membrane so that the antibody can no longer move from its position on the support. The first antibody is a capture antibody, and constitutes a detection section by being immobilized on the support. As used herein, "detection section" refers to a site where the presence of an antigen is detected by capturing the sample antigen which is attached to or attaches to the second antibody.

The support membrane may be of any material which allows the first antibody to be immobilized through electrostatic interactions, hydrophobic interactions or chemical coupling and on which substances such as the sample and the second antibody can move to the detection site. Examples of suitable support membranes include nitrocellulose, polyvinylidene difluoride (PVDF), and cellulose acetate.

In a preferred embodiment, the support membrane comprises a control section for checking whether the sample has developed properly. A substance that can to bind to a control substance is immobilized on the control section. The locations of the detection section and the control section on the support are not particularly limited. Typically, the control section is downstream of the detection section.

In the test device of the present invention, a liquid sample dropped onto the sample addition section of the device wicks towards a section of the device which comprises the second antibody, and the mixture of the sample and the labeled antibody migrate through the support membrane, and the signal develops at the detection site (see FIG. 1A). The antigen and the labeled antibody form an immunocomplex when the sample contains Dps. At the detection section, the first antibody captures the complex through an antigen-antibody interaction, and the conjugate accumulates and develops color. The presence or absence of antigen in the sample can then be determined by visually checking the extent of the color at the detection section. When the support has a control section, the test device may further comprise a control labeled substance in or adjacent to the section of the device which comprises the second antibody. The control labeled substance can be captured by a substance that can bind the control labeled substance at the control section, and the control labeled substance accumulates and develops color. When the second antibody is also used as a control labeled substance, the residual second antibody that did not form a complex with the antigen in the sample passes through the detection site, and is captured by a substance that is immobilized at the downstream control section. The labeled antibody accumulates and develops color.

In one embodiment, the first antibody is the antibody of the present invention, i.e. any one of the antibody embodiments disclosed previously. In an alternative embodiment, the second antibody is the antibody of the present invention. In a preferred embodiment, both the first and the second antibody are the antibody of the present invention. More preferably, the first and second antibody comprise a light chain variable region (VL) and a heavy chain variable region (VH), wherein said VL comprises LCDR1, LCDR2 and LCDR3 polypeptides and VH comprises HCDR1, HCDR2 and HCDR3 polypeptides, wherein LCDR1 is SASSSVSS-SYLH (SEQ ID NO: 1), LCDR2 is RTSNLAS (SEQ ID NO: 2), LCDR3 is QQWSGYPFT (SEQ ID NO: 3), HCDR1 is GFSLTSSGVH (SEQ ID NO: 4), HCDR2 is VIWRGGST-DYNAAFMS (SEQ ID NO: 5) and HCDR3 is NYYYGT-SPDYFDY (SEQ ID NO: 6). Even more preferably, the first and second antibody comprise a VL and a VH, wherein the VL is SEQ ID NO: 7 and the VH is SEQ ID NO: 8. Most preferably, the first and second antibody comprise a LC and a HC, wherein the LC is SEQ ID NO: 9 and the HC is SEQ ID NO: 10.

In a preferred embodiment, the second antibody is labeled, preferably with a colored synthetic polymer particle and/or a colloidal metal particle. More preferably, the second antibody is labeled with a colored synthetic polymer particle.

Method

In a third aspect, the present invention provides a method for detecting bacteria of the genus *Campylobacter* in an isolated sample which comprises contacting the sample with the test device of the present invention.

In a preferred embodiment, the bacteria of the genus *Campylobacter* is of the species *Campylobacter jejuni* and/or *Campylobacter coli*.

In a preferred embodiment, the isolated sample is an isolated stool sample. The stool sample may be prepared by dispersing a stool sample in a pH 8.4 Tris-base buffer before contacting the sample with the test device of the present invention.

Uses of the Antibody

In a fourth aspect, the present invention provides the use of the antibody of the present invention for the detection of bacteria of the genus *Campylobacter*. Preferably, the bacteria of the genus *Campylobacter* is of the species *Campylobacter jejuni* and/or *Campylobacter coli*.

In a preferred embodiment, the antibody of the present invention is used to detect bacteria of the genus *Campylobacter* in a stool sample. Preferably, the bacteria of the genus *Campylobacter* is of the species *Campylobacter jejuni* and/or *Campylobacter coli*.

In a fifth aspect, the preset application provides the use of the antibody of the present invention for the manufacture of an immunoassay test device. The term "immunoassay test device" can refer to any test device which comprises at least one antibody. Examples of test devices include immunochromatographic test devices, ELISA test devices, and immunoprecipitation test devices. The immunoassay test device may then be used in a method for detecting bacteria of the genus *Campylobacter* in an isolated sample which comprises contacting the sample with the immunoassay test device. Preferably, the bacteria of the genus *Campylobacter* is of the species *Campylobacter jejuni* and/or *Campylobacter coli*. More preferably, the bacteria of the genus *Campylobacter* is of the species *Campylobacter jejuni* and/or *Campylobacter coli* and the isolated sample is an isolated stool sample.

In a preferred embodiment, the antibody of the present invention is used to manufacture the immunochromatographic test device of the present invention.

Hybridoma

In a sixth aspect, the present invention provides a hybridoma which produces the antibody of the present invention.

Monoclonal antibodies can be generated by immunizing mice with a Dps-derived antigen. Splenocytes from these mice immunized with the antigen of interest are used to produce hybridomas that secrete mAbs with specific affinities for epitopes (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

EXAMPLES

Example 1

Production of Monoclonal Antibodies which Specifically Bind Dps

The CL30Camp monoclonal antibody was obtained from the hybridoma of the same name. Briefly, a hybridoma which produces the monoclonal antibody CL30Camp was obtained by performing standard protocols known in the art (KÖHLER G Milstein C Continuous cultures of fused cells secreting antibody of predefined specificity Nature Aug. 7, 1975 0028-0836 256 5517 495-497).

BALB/c type mice were immunized with purified, native Dps (the purified, native Dps was obtained through the methods described in Ishikawa et al., 2003. J. *Bacteriol*. 185(3): 1010-1017). Lymphocytes from immunized mice were fused with a myeloma cell line, specifically a SP20 cell line, and the hybridomas that were obtained were screened by ELISA to find clones which produce antibodies that bind to Dps. To perform the ELISA, wells of a 96 well microtiter plate were coated with a rabbit polyclonal anti-Dps antibody in 100 mM carbonate buffer pH 9 at 37° C. for 2 h. The wells were washed and then a Dps solution in PBS containing 1% (w/v) BSA (bovine serum albumin) was added. The wells were washed again and then the supernatant of a hybridoma cell line culture was added to each well. The presence of antibody which can bind to the Dps was revealed using an anti-mouse IgG peroxidase conjugate (Sigma-Aldrich) and the corresponding substrate.

The hybridomas which secreted antibodies with high specificity and affinity for Dps were selected. Among the selected hybridomas, the ones that produced good titers of antibody which performed favorably in thermal stress tests were further selected.

The antibodies were purified using Protein A affinity chromatography using methods which are common in the art (see the "*Affinity Chromatography Vol.* 1: *Antibodies*" handbook 18103746 AF published on April 2016 by GE Healthcare Bio-Sciences AB).

CL30Camp was selected because it had high specificity and sensitivity in ELISA tests as well as in immunochromatography tests (Table 1, the sample used was PBS containing 0.1% (w/v) BSA).

TABLE 1

Studying the background noise of different combinations of isolated antibodies

| | CL18Camp | CA29 | CL30Camp | CA32 Labeled |
|---|---|---|---|---|
| CL18Camp | +/− | +/− | — | +/− |
| CA29 | + | + | +/− | + |
| CL30Camp | — | — | — | +/− |
| CA32 Immobilized | +/− | +/− | +/− | + |

Example 2

Preparation of the Conjugated Antibody

Anti-Dps antibodies were labeled with colored polystyrene nanoparticles (K1 020 Estapor®, Merck, Darmstadt, Germany). The colored nanoparticles comprised carboxyl groups on the surface and had an average diameter of around 300 nm. The antibodies were labeled as follows: a 1 mL solution containing 10% (w/v) particles was washed, centrifuged and resuspended in a 10 mM MES (2-(N-morpholino) ethanesulfonic acid) buffer with a pH of 6.0. EDC (1-ethyl-3-(3-dimethylaminopropyl) carbodiimide) was then added to a final concentration of 5 mM. The solution was incubated for 1 hour at 37° C. and then excess reagent was removed by centrifuging the solution and removing the supernatant.

The activated particles were resuspended in 10 mM MES pH 6 and the antibody was added to a surface concentration of 2 mg/m$^2$. The solution was then incubated for 4 hours at 25° C. and the labeled antibodies were then washed with a solution containing 0.1% (w/v) Tween-20. The labeled antibodies were diluted in a 0.05% (w/v) Tris (tris (hydroxymethyl)aminomethane) pH 8.0 buffer solution containing 10% (w/v) sucrose, 2% (w/v) BSA, 1% (w/v) PEG-6000 and 2% (w/v) Tween-20.

This solution was deposited at a rate of 15 μl/cm on woven polyester fibers with a width of 29 mm. The polyester fibers were dried for 24 hours in a chamber at 30° C. and 20% relative humidity.

Example 3

Preparation of the Detection and Control Sections

A PBS buffer containing 1 mg/mL of anti-Dps antibody was deposited in a linear fashion on a nitrocellulose membrane which had a laminated width of 25 mm and a pore size of between 10 and 30 microns. The antibody solution was deposited at a rate of 1 μL/cm. The membrane was then dried for 24 hours in a chamber at 30° C. and 20% relative humidity.

Polyclonal rabbit anti-mouse IgG was deposited on the control section in parallel to the deposit of the anti-Dps antibody on the detection section. The same conditions were used for the deposit of the Polyclonal rabbit anti-mouse IgG on the nitrocellulose membrane.

Example 4

Assembly of the Immunochromatographic Test Device

The conjugate material (sample addition section and section which comprises the labeled antibody), support membrane and the absorbent material was assembled as indicated in FIGS. 1B and 1C on a plastic support with an adhesive foil. The strips were transversely cut to a width of 4 mm.

The solution used for dispersing stool samples consisted of an aqueous solution of 200 mM Tris buffer with a pH of 8.4. This dispersion solution was dispensed in vials for sampling. Each vial contained 1 mL of solution.

Example 5

Limit of Detection of the Test Device for Dps of *C. jejuni* and *C. coli*

½ serial dilutions of Dps were prepared in the dispersion solution described above. 100 μl of a sample was applied to an immunochromatographic test device of the invention. The test device was allowed to develop for 10 minutes at room temperatures before the results were visually assessed. The same experiment was performed by diluting Dps in stool samples dispersed in the same buffer. The results are shown in Tables 2 and 3. Interpretation: +=positive response; −=negative response; +/−=weak positive response.

TABLE 2

Limit of detection of the test device for Dps of *C. jejuni*

| | 1.85 ng/mL | 0.92 ng/mL | 0.46 ng/mL | 0.23 ng/mL | 0.115 ng/mL | 0.057 ng/mL |
|---|---|---|---|---|---|---|
| CL30Camp/CL30Camp | + | + | + weak | − | − | − |

TABLE 3

Limit of detection of the test device for Dps of *C. coli*

| | 3 ng/mL | 1.5 ng/mL | 0.75 ng/mL | 0.375 ng/mL | 0.187 ng/mL |
|---|---|---|---|---|---|
| CL30Camp/CL30Camp | + | + weak | +/− | — | — |

Example 6

Detection of False Positives 20 mg of stool sample which was shown to be positive or negative for *C. coli* or *C. jejuni* was dispersed in 1 mL of the dispersion solution described in Example 4. 100 μl of a sample was applied to an immunochromatographic test device of the invention. The test device was allowed to develop for 10 minutes at room temperatures before the results were visually assessed. Interpretation: +=positive response; −=negative response; +/−=weak positive response.

TABLE 4

Reactivity of the test device with samples containing no *C. jejuni* or *C. coli*

| | Negative samples | | | | | | | | | |
|---|---|---|---|---|---|---|---|---|---|---|
| | 10690 | 11485 | 4471 | 11160 | 4488 | 10726 | 4468 | 4484 | 4466 | 10770 10977 |
| CL30Camp/CL30Camp | — | — | — | — | — | — | — | — | — | — |

TABLE 5

Reactivity of the test device with samples containing *C. jejuni* or *C. coli*

| | Positive samples | | | | | 5 |
|---|---|---|---|---|---|---|
| | 3626 | 3628 | 3640 | 3631 | 3622 | |
| CL30Camp/CL30Camp | + | + | + | + | + | |

The invention claimed is:

1. A monoclonal antibody comprising a light chain variable region (VL) and a heavy chain variable region (VH), wherein said VL comprises LCDR1, LCDR2 and LCDR3 polypeptides and VH comprises HCDR1, HCDR2 and HCDR3 polypeptides, wherein LCDR1 is SASSSVSS-SYLH (SEQ ID NO: 1), LCDR2 is RTSNLAS (SEQ ID NO: 2), LCDR3 is QQWSGYPFT (SEQ ID NO: 3), HCDR1 is GFSLTSSGVH (SEQ ID NO: 4), HCDR2 is VIWRGGST-DYNAAFMS (SEQ ID NO: 5) and HCDR3 is NYYYGT- SPDYFDY (SEQ ID NO: 6) and specifically binds Dps (DNA-Binding Protein from Starved Cells) of *Campylobacter coli* or *Campylobacter jejuni*, or both.

2. The antibody according to claim 1, wherein the antibody comprises a VL and a VH, wherein the VL is SEQ ID NO: 7 and the VH is SEQ ID NO: 8.

3. The antibody according to claim 1, wherein the antibody comprises a light chain (LC) and a heavy chain (HC), and the LC is SEQ ID NO: 9 and the HC is SEQ ID NO: 10.

4. A hybridoma which produces the antibody according to claim 1.

5. An immunochromatographic test device comprising:
(a) a first antibody as defined in claim 1 which specifically binds to Dps (DNA-Binding Protein from Starved Cells);
(b) a second antibody as defined in claim 1 which specifically binds to Dps (DNA-Binding Protein from Starved Cells); and
(c) a support membrane,
wherein the first antibody is immobilized on the support membrane and the second antibody is labeled and wherein the first antibody or the second antibody, or both, is a monoclonal antibody and specifically binds DNA-Binding Protein from Starved Cells (DPs) of *Campylobacter coli* or *Campylobacter jejuni*, or both.

6. The immunochromatographic test device according to claim 5, wherein the second antibody is labeled with a colored synthetic polymer particle or a colloidal metal particle, or both.

7. The immunochromatographic test device according to claim 5, wherein the antibody is labeled with a colored synthetic polymer particle comprising polystyrene.

8. The immunochromatographic test device according to claim 5, wherein the first antibody or the second antibody, or both, comprises a VL and a VH, wherein the VL is SEQ ID NO: 7 and the VH is SEQ ID NO: 8.

9. The immunochromatographic test device according to claim 5, wherein the first antibody or the second antibody, or both comprises a light chain (LC) and a heavy chain (HC), and the LC is SEQ ID NO: 9 and the HC is SEQ ID NO: 10.

10. A method for detecting bacteria of the genus *Campylobacter* in an isolated sample, comprising contacting the sample with the immunochromatographic test device according to claim 5.

11. The method according to claim 10, wherein the bacteria of the genus *Campylobacter* is *Campylobacter jejuni* or *Campylobacter coli*, or both.

12. The method according to claim 10, wherein the isolated sample is an isolated stool sample.

* * * * *